(12) United States Patent
Jubinsky et al.

(10) Patent No.: US 8,581,005 B2
(45) Date of Patent: Nov. 12, 2013

(54) MITOCHONDRIAL INHIBITORS TO TREAT HUMAN DISEASE

(75) Inventors: Paul Jubinsky, Hyde Park, NY (US); Bhaskar C. Das, West Nyack, NY (US); Mary K. Short, Hyde Park, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 193 days.

(21) Appl. No.: 13/263,083

(22) PCT Filed: Mar. 16, 2010

(86) PCT No.: PCT/US2010/000787
§ 371 (c)(1),
(2), (4) Date: Dec. 1, 2011

(87) PCT Pub. No.: WO2010/120337
PCT Pub. Date: Oct. 21, 2010

(65) Prior Publication Data
US 2012/0093728 A1    Apr. 19, 2012

Related U.S. Application Data

(60) Provisional application No. 61/212,571, filed on Apr. 13, 2009.

(51) Int. Cl.
*C07C 233/78*   (2006.01)
*A61K 31/165*   (2006.01)

(52) U.S. Cl.
USPC ........ 564/181; 544/105; 549/406; 514/230.5; 514/456; 514/617

(58) Field of Classification Search
USPC ............ 564/181; 544/105; 549/406; 514/617
See application file for complete search history.

(56) References Cited

U.S. PATENT DOCUMENTS 8,460,635 B2 *   6/2013   Kalpana et al. .............. 424/1.11

OTHER PUBLICATIONS

Das B C et al., entitled "Design, synthesis of novel peptidomimetic derivatives of 4-HPR for rhabdoid tumors," Bioorganic & Medicinal Chemistry Letters 18 (2008), pp. 4177-4180.
Ekelund S et al., entitled "Guanidino-containing drugs in cancer chemotherapy: biochemical and clinical pharmacology," Biochemical Pharmacology 61 (2001), pp. 1183-1193.
PCT International Search Report dated Aug. 19, 2010 in connection with PCT International Patent Application No. PCT/US2010/00787, 6 pages.
PCT Written Opinion of the International Searching Authority dated Aug. 19, 2010 in connection with PCT International Patent Application No. PCT/US2010/00787, 6 pages.

* cited by examiner

*Primary Examiner* — Shailendra Kumar
(74) *Attorney, Agent, or Firm* — Amster, Rothstein & Ebenstein LLP

(57) ABSTRACT

The present invention relates to inhibitors of mitochondria-associated, granulocyte-macrophage colony stimulating factor signaling molecule (Magmas), and related compositions and uses thereof.

14 Claims, 4 Drawing Sheets

A                                           B

MITOCHONDRIAL INHIBITORS TO TREAT HUMAN DISEASE

CROSS-REFERENCE TO RELATED APPLICATIONS

This application is a U.S. national stage entry under 35 U.S.C. §371 of PCT International Patent Application No. PCT/US2010/000787, filed Mar. 16, 2010, and claims priority to U.S. Provisional Patent Application No. 61/212,571, filed Apr. 13, 2009, the contents of which are incorporated herein by reference in their entirety.

FIELD OF THE INVENTION

The present invention relates to inhibitors of mitochondria-associated, granulocyte-macrophage colony stimulating factor signaling molecule (Magmas), and related compositions and uses thereof.

BACKGROUND OF THE INVENTION

Throughout this application various publications are referred to by Arabic numerals in superscript. Full citations for these references may be found at the end of the specification immediately preceding the claims. The disclosures of these publications are hereby incorporated by reference in their entireties into the subject application to more fully describe the art to which the subject application pertains.

Mitochondria are organelles that influence nearly every important cellular process including metabolism, transcription and translation, survival, growth and differentiation. Regulation of these processes is beneficial in a variety of pathological states in which mitochondria contribute to the pathogenesis or maintenance of a disease. This includes those that may have multi-factorial etiologies such as cancer or aging.

Magmas (Mitochondria associated granulocyte-macrophage colony stimulating factor signaling molecule), a granulocyte-macrophage colony stimulating factor (GM-CSF) inducible gene, has been identified in myeloid cells[1]. Magmas mRNA expression was observed in all tissues examined[1]. Magmas protein localizes to the inner membrane of mitochondria, and protein expression is both developmentally regulated and tissue specific[2]. The protein is highly conserved, and is required for mitochondria function and cell survival[3]. Immuno-precipitation and immuno-affinity chromatography studies show that Magmas mostly interacts with other mitochondrial proteins. Impairment of Magmas function differentially affects complex IV activity, leading to loss of mitochondrial membrane potential.

Magmas expression in prostate cancer samples suggested a role for this protein in human cancer[4]. Magmas staining is minimal to absent in normal prostate tissue by immuno-histochemistry. Elevated levels of Magmas protein occurred in a subset of advanced-grade, invasive adenocarcinoma. However, many samples of similar stage had staining patterns identical to normal prostate epithelium. Increased staining resulted from higher amounts of Magmas in the abnormal cells and not from increased numbers of mitochondria. Since not all patients with morphological high-grade prostate cancer do poorly, one possibility is that Magmas expression may affect therapeutic response to therapy, possibly by altering mitochondrial function. Data from independent laboratories showing that Magmas mRNA expression correlates with survival in several human tumors (breast,[10,11] colon and lung) is consistent with this theory.

Based on the discovery of Magmas and its role in mitochondrial activity, there is a pressing need for compounds capable of manipulating such activity by inhibiting Magmas in cells. The present invention addresses this need.

SUMMARY OF THE INVENTION

The invention provides compounds which bind to mitochondria-associated, granulocyte-macrophage colony stimulating factor signaling molecule (Magmas) and inhibit mitochondrial activity.

The invention provides compounds of formula (I) and formula (II):

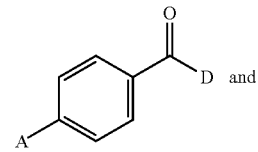

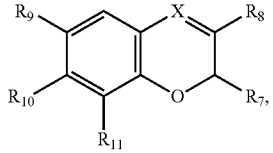

where the variables are defined herein below.

The invention also provides pharmaceutical compositions comprising any of the compounds described herein and a pharmaceutically acceptable carrier.

The present invention is further directed to methods for (i) inhibiting mitochondrial activity in a cell or tissue, (ii) inhibiting metabolism in a cell or tissue, or (iii) detecting the presence of mitochondria-associated, granulocyte-macrophage colony stimulating factor signaling molecule (Magmas) in a cell or tissue, comprising contacting the cell or tissue with any of the compounds disclosed herein, as discussed more fully below.

The present invention is further directed to a method for treating cancer and other diseases in a subject comprising administering to the subject a therapeutically effective amount of the any of the compounds disclosed herein.

DETAILED DESCRIPTION OF THE INVENTION

Figure 1:
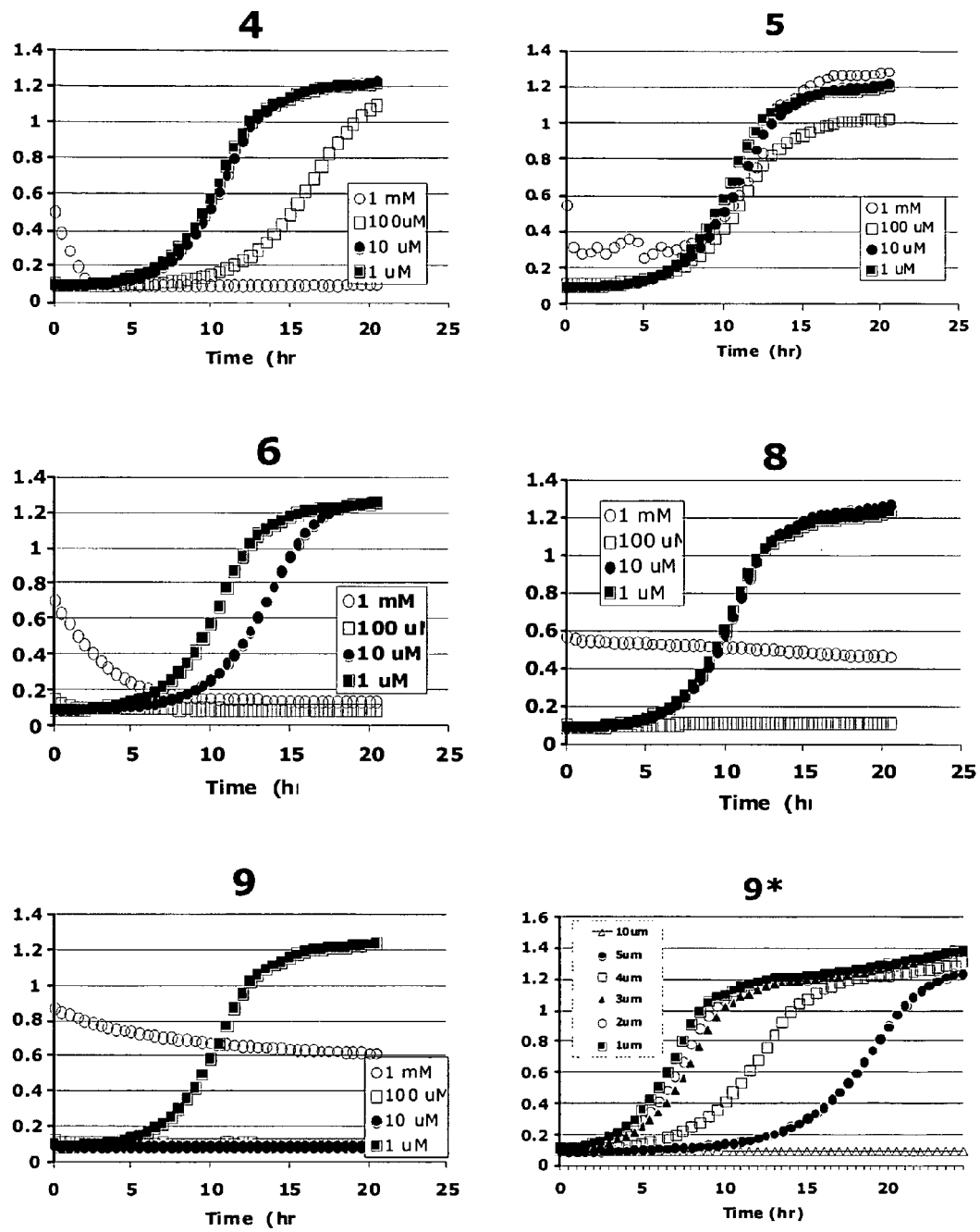
FIG. 1. Dose response to Magmas small molecule inhibitors on yeast proliferation. Data shown for Compounds 4, 5, 6, 8 and 9. 9* indicates results obtained with low concentrations of Compound 9.

The present invention provides compounds that affect mitochondrial activity associated with Magmas (mitochondria associated granulocyte-macrophage colony stimulating factor signaling molecule). Examples of such compounds include small molecule inhibitors (SMI) that bind to Magmas and inhibit its activity.

The invention provides a compound of formula (I):

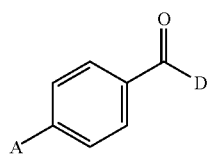

(I)

wherein A is

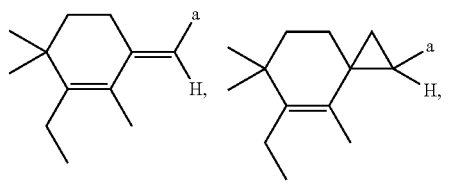

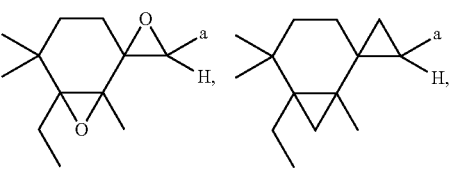

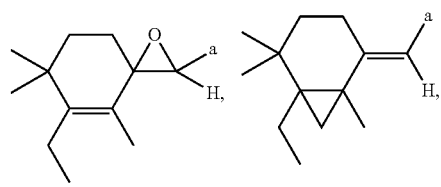

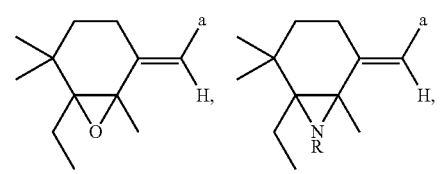

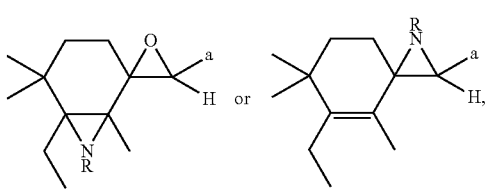

where "a" represents the point of attachment of A to the ring structure of formula (I) and where R is H, aliphatic, aromatic or heterocyclic; and wherein D is

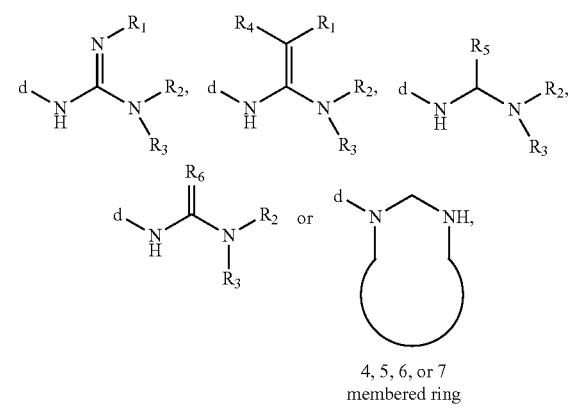

4, 5, 6, or 7 membered ring where "d" represents the point of attachment of D to the carbon atom of C=O of formula (I); where $R_1$, $R_2$, $R_3$, $R_4$ and $R_5$ are independently H, alkyl, aryl, phenyl, heteroaryl, arylalkyl, heterocyclic, alkenyl, allene, Br, Cl, I, F, OH, $NO_2$, $OCH_3$, $OC_2H_5$, O-alkyl, SH, S-alkyl, $NH_2$, or NH-alkyl; and where $R_6$ is C, O or S; or a pharmaceutically acceptable salt thereof.

Preferably, the compound of formula (I) has the formula:

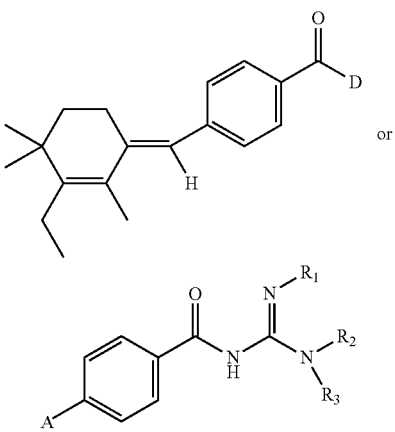

or a pharmaceutically acceptable salt thereof, where A, D, $R_1$, $R_2$ and $R_3$ are as previously defined.

More preferably, the compound of formula (I) has the formula:

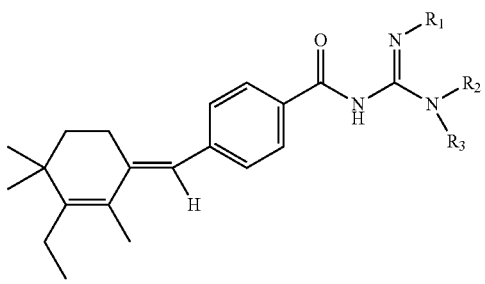

or a pharmaceutically acceptable salt thereof, where $R_1$, $R_2$ and $R_3$ are as previously defined.

Preferably, R=H. Preferably, in formula (I), alky is C1-C3 alkyl. Preferably, one or more of $R_1$, $R_2$, $R_3$, $R_4$ and $R_5$ is H.

A preferred compound of formula (I) has the structure:

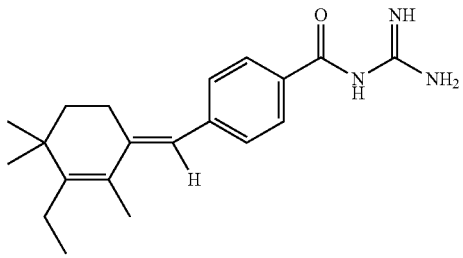 [SMILES: CCC1=C(C)/C(=C/c2ccc(C(=O)NC(=N)N)cc2)CCC1(C)C]

or a pharmaceutically acceptable salt thereof.

The invention also provides a compound of formula (II):

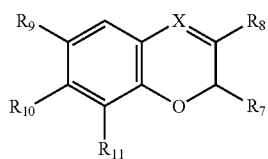

wherein X is C or N; $R_7$ and $R_8$ are independently H, phenyl, aryl, heteroaryl, heterocyclic or C1-10 alkyl; $R_9$, $R_{10}$ and $R_{11}$ are independently H, Br, Cl, I, F, OH or $NO_2$; or a pharmaceutically acceptable salt thereof.

Preferably, when one of $R_7$ or $R_8$ is phenyl, the other is H. Preferably, when $R_9$ is Br, Cl, I or F, then $R_{10}$ and $R_{11}$ are each H.

Preferably, when $R_8$, $R_{10}$ and $R_{11}$ are each H, X is C, and $R_7$ is phenyl, then $R_9$ is not $NO_2$.

A preferred compound of formula (II) has the structure:

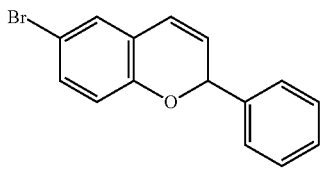

or a pharmaceutically acceptable salt thereof.

Pharmaceutically acceptable salts are non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

The compounds of the present invention can be labeled with a detectable marker. Labeling may be accomplished using one of a variety of labeling techniques, including peroxidase, chemiluminescent, and/or radioactive labels known in the art. The detectable marker may be, for example, a nonradioactive or fluorescent marker, such as biotin, fluorescein (FITC), acridine, carboxy-X-rhodamine or cholesterol, which can be detected using fluorescence and other imaging techniques readily known in the art. Alternatively, the detectable marker may be a radioactive marker, including, for example, a radioisotope. The radioisotope may be any isotope that emits detectable radiation, such as, for example, $^{35}S$, $^{32}P$, $^{3}H$, $^{18}F$, $^{34m}Cl$, $^{75}Br$, $^{76}Br$, $^{120}I$, $^{122}I$, $^{123}I$, $^{124}I$, $^{125}I$, or $^{131}I$.

The invention provides methods for detecting the expression or presence of mitochondria-associated, granulocyte-macrophage colony stimulating factor signaling molecule (Magmas) in a tissue or cell comprising contacting the tissue or cell with any of the compounds disclosed herein that include a detectable marker. Many suitable markers and methods for detecting the markers are known in the art. For example, radioactivity emitted by a radioisotope can be detected by techniques well known in the art. For example, gamma emission from the radioisotope may be detected using gamma imaging techniques, particularly scintigraphic imaging. In a preferred embodiment of the present invention, the presence of Magmas in a cell or tissue can be determined via positron emission topography (PET) imaging. PET is well known in the art and involves measuring emissions from radioactively labeled metabolically active chemicals that have been injected into the bloodstream. Through PET, the presence of Magmas in a cell or tissue can be detected by detecting the presence of any of the radiolabeled compounds described herein which have bound to Magmas in the cell or tissue. PET methods are described in U.S. Pat. Nos. 7,402,807 and 7,321,122, the contents of which are hereby incorporated in their entirety into the subject application. In one embodiment, the cell or tissue is in a subject, preferably a human. The labeled compounds can be used, for example, to identify tissues that overexpress Magmas, to image ischemic injury, to monitor the course of disease treatment, and to predict the response of subjects to chemotherapy.

The present invention further provides pharmaceutical compositions comprising any of the compounds described herein and a pharmaceutically acceptable carrier. As used herein, a "pharmaceutically acceptable" carrier shall mean a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, sterile isotonic saline, water, and emulsions such as, for example, oil/water emulsions and microemulsions.

The present invention further provides methods for inhibiting mitochondrial activity in a cell or tissue comprising contacting the cell or tissue with any of the compounds described herein. As used herein, "mitochondrial activity" shall mean any normal activity associated with mitochondria. Examples of mitochondrial activity include, but are not limited to, ATP production, regulation of cellular metabolism, storage of calcium ions, regulation of the membrane potential, apoptosis, calcium signaling, regulation of cell proliferation, steroid synthesis, and certain heme synthesis reactions. In one embodiment, the cell or tissue is in a subject, preferably a human.

The present invention further provides methods for inhibiting metabolic activity in a cell or tissue comprising contacting the cell or tissue with any of the compounds described herein. As used herein, "metabolic activity" shall mean either catabolism or anabolism associated with the normal function of mitochondria in a cell. In one embodiment, the cell or tissue is in a subject, preferably a human. The present invention may be used to slow the biological effects of aging, which are achieved, for example, by reducing metabolic activity.

The present invention further provides methods for treating cancer in a subject comprising administering to the subject a therapeutically effective amount of any of the compounds described herein. The cancer to be treated can include, but is not limited to, cervical carcinoma, hepatocellular carcinoma, a lymphoma, Burkitt's lymphoma, nasopharangeal carcinoma, Hodgkin's disease, skin cancer, primary effusion lymphoma, multicentric Castleman's disease, T-cell lymphoma, B-cell lymphoma, splenic lymphoma, Kaposi's sarcoma, post-transplant lymphoma, brain cancer, osteosarcoma, mesothelioma cervical dysplasia, anal cancer, colorectal cancer, cervical cancer, vulvar cancer, vaginal cancer, penile cancer, oropharyneal cancer, nasopharyneal cancer, oral cancer, liver cancer, renal cancer, melanoma, adult T-cell leukemia, hairy-cell leukemia, breast cancer, colon cancer, lung cancer, and prostate cancer. Preferred cancers include breast cancer, lung cancer, prostate cancer and osteosarcoma. In the preferred method, the subject is a human. The Magmas inhibitors disclosed herein can be used in combination with standard chemotherapies.

The present invention further provides a method for treating immune dysfunction, inflammation or disease characterized by rapid proliferation of blood vessels in a subject comprising administering to the subject a therapeutically effective amount of any of the compounds described herein. These conditions include, for example, rheumatologic disorders, graft-versus-host disease (GVHD), autoimmune disease, respiratory distress syndrome (ARDS), sepsis related hypotension, and diabetic- and oxygen-induced retinopathies.

The compounds of the present invention can be administered to subjects using routes of administration known in the art. The administration can be systemic or localized to a tumor site. Routes of administration include, but are not limited to, intravenous, intramuscular, intrathecal or subcutaneous injection, oral or rectal administration, and injection into a tumor site.

The invention also provides for the use of any of the compounds disclosed herein for treating a subject with cancer or other disease, inhibiting mitochondrial activity in a cell, inhibiting metabolism in a cell or detecting the presence of mitochondria-associated, granulocyte-macrophage colony stimulating factor signaling molecules in a cell, and for the use of any of the compounds disclosed herein for the preparation of a composition for treatment of cancer or other disease, inhibiting mitochondrial activity in a cell, inhibiting metabolism in a cell or detecting the presence of mitochondria-associated, granulocyte-macrophage colony stimulating factor signaling molecules in a cell.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

The inventors hypothesized that small molecule inhibitors (SMI) of Magmas could be beneficial for studying mitochondrial function and for diagnosing and treating human disease. Small molecules were devised to interact with highly conserved regions of the molecule. A small chemical library of compounds (Table 1) containing oxazine, chromene and gudanidine pharamacophore groups was synthesized. The biological activity of the compounds was tested in *Sacchromyces cerevisae* proliferation assays. Human and yeast Magmas share 42% identity at the level of amino acid resides and human Magmas is able to functionally replace the yeast homolog.

TABLE 1

Library of compounds synthesized.

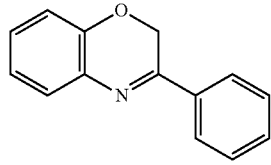 [SMILES: c1ccc(C2=Nc3ccccc3OC2)cc1]
(1)

(2)

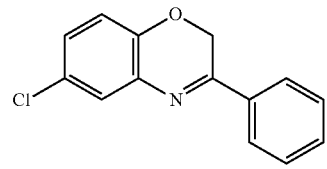 [SMILES: Clc1ccc2c(c1)N=C(c1ccccc1)CO2]
(3)

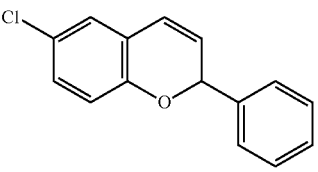 [SMILES: Clc1ccc2c(c1)C=CC(c1ccccc1)O2]
(4)

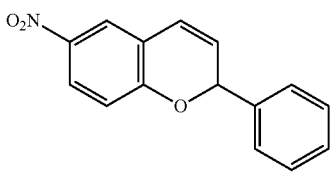 [SMILES: O=[N+]([O-])c1ccc2c(c1)C=CC(c1ccccc1)O2]
(5)

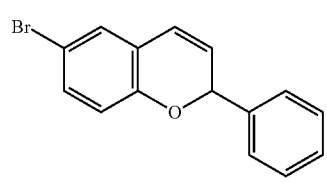
(6)

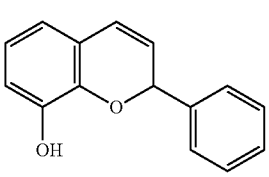 [SMILES: Oc1cccc2c1OC(c1ccccc1)C=C2]
(7)

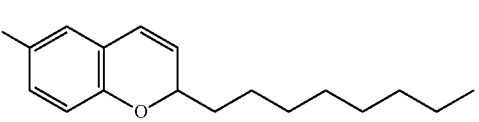
(8)

TABLE 1-continued

Library of compounds synthesized.

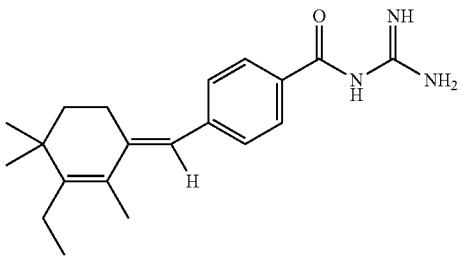 [SMILES: CCC1=C(C)/C(=C/c2ccc(C(=O)NC(=N)N)cc2)CCC1(C)C]

(9)

Synthesis of Compound 9

Compound 9 was synthesized by chemical modification of existing reactions. The synthesis of 9 involves the reaction with methyl magnesium bromide with β-cyclocitral in THF to give alcohol as a yellow oil.[5] The alcohol gave satisfactory spectral data and was directly converted to triphenyl phosphine salt by treatment with triphenylphosphine hydrobromide in methanol. Recrystallization of salt from methanol/ether (1:6) gave a yellow crystalline solid[6]. Formation of the Witting reagent from salt in ether was accomplished with n-butyllithium in hexane at room temperature (dark-red color), then the Witting reagent was treated with methyl 4-formybenoate in ether at −78° C. for 10-15 minutes and then stirred at room temperature under a nitrogen atmosphere for 30 hrs. After work up, crude ester was purified by flash column chromatography (hexane/ethyl acetate: 98/2) to give a brown oil in 85% yield[7]. The ester was saponified to generate a white solid that was filtered, washed with water, and dried. The product was recrystallized from hot ethanol and washed with dry hexane to give acid as white crystals (87%) yield. The structure was confirmed by $^1$H, $^{13}$C NMR and NOE experiment, HMBC, and HRMS. The acid was converted to chloride in the presence of oxalyl chloride, then reacted with guanidine hydrochloride, 1,1' carbonyldiimidazole in DMF-dioxane mixture. The crude reaction mixture was evaporated, the residue was purified by fractional crystallization from methanol to give compound 9 white crystals mp165-167° C.[8,9].

More specifically, a mixture of acid (300 mg, 1.05 mmol) in dry DMF (4 mL) and CDI (171 mg, 1.05 mmol) was stirred at room temperature under nitrogen atmosphere for 1 h. Guanidine base was prepared by consecutive addition of sodium-tert-butoxide (201.8 mg, 2.1 mmol) and guanidine hydrochloride (200 mg, 2.1 mmol) to a dry mixture of dimethylformamide/dioxane (1:1, 8 mL) under nitrogen atm, this mixture was heated to 50-55° C. for 20 min, and then NaCl was filtered. The solution of CDI and acid was added to the guanidine base solution, then the mixture was stirred at room temperature for 6 h. The progress of the reaction was monitored, the reaction mixture was evaporated, and DMF removed under vacuum. The residue was suspended in cold water (8 mL). The crystalline solid was filtered, washed with water, and dried, then purified by fractional crystallization from methanol to give white solid 340 mg (87%). mp: 165-167° C. $^1$H-NMR (300 MHz, Acetone-d6): δ 7.90-7.82 (d, J=8.0 Hz, 2H), 7.40 (d, J=8 Hz, 2H), 6.47 (s, 1H), 2.55 (m, 2H), 2.19 (q, 3H), 1.86 (s, 3H), 1.44 (m, 2H), 1.05 (s, 6H) and 1.03 (t, J=8 Hz, 3H) $^{13}$C NMR CDCl$_3$: δ 177.2, 163.8, 147.6, 141.5, 140.9, 137.2, 129.06, 128.7, 127.5, 121.6, 39.1, 35.9, 28.6, 27.5, 24.4, 22.9, 14.9 and 14.6 ESI MS: calculated for $C_{20}H_{27}N_3O$ ([M+H]$^+$) 326.2227. found: 326.2223.

Synthesis of Additional Compounds

Since lead compound 9 contains amide derivatives of guanidine, structure activity relationships can be determined by taking different substituents of guanidine, then by amide coupling to obtain varieties of guanidine substituted analogues. In addition, thioguanidine derivatives can be synthesized by taking acids and doing amide coupling with thioguanidine derivatives. Since lead compound 9 contains two double bonds, additional related structures can be synthesized through selective epoxidation, aziridination and cyclopropanation reactions.

Magmas Mutagenesis and Expression

Mutations in Magmas were introduced by error prone PCR and the changes were identified by sequencing. Only genes with a single amino acid change were further analyzed. The genes encoding the mutations were spliced into plasmid pRS315 containing the selectable antibiotic resistance marker (leu) and transfected into yeast where the wt genomic copy was replaced by a his cassette and the essential Magmas activity was maintained by wt Magmas in the plasmid pRS316 (ura). The plasmid containing the wt Magmas gene was lost by selection in media containing FOA, resulting in yeast strains only expressing the mutant gene. Total yeast protein from each of the strains was separated by SDS-PAGE, and transferred to nitrocellulose membranes. The membranes were sequentially incubated with rabbit anti-Magmas antibody, HRP conjugated goat anti-rabbit antibody and chemiluminescence reagent. The signal was captured with a Fujifilm LAS-3000 Imager and the data analyzed with ImageGage software.

In vitro Cell Proliferation Assay

Sacchromyces cerevisiae strain J47D in log phase growth, was plated in 96 well dishes at 1.5×10$^4$ cells/well in YEPD media. Magmas inhibitors were diluted in DMSO and added at various concentrations (range 0 mM to 1 mM) to each well in triplicate at a final DMSC concentration of 1%. Samples were cultured at 30° C. in a Bioscreen C MBR incubator (Growth Curves USA, Piscataway, N.J.) and optical density (OD) readings were measured every 30 minutes for the indicated time in the plots. Cell proliferation data was analyzed and plotted using Microsoft Excel. Standard deviations were smaller than 2% of the mean OD value (n=3), and each experiment was performed at least two independent times.

Results and Discussion

Reduced Magmas function caused by siRNA knockdown or by mutations in Magmas causes growth inhibition and cell cycle arrest. To assay whether the compounds were active, their ability to inhibit yeast proliferation was measured. The results obtained in yeast are equivalent to those found in mammalian cells in part because the human homolog is fully functional in yeast and the target region is identical across all eukaryotic species.

Concentration effects of the compounds on yeast proliferation are shown in FIG. 1. Elevated OD at early time points and minimal changes over time indicates that the compound is insoluble at that concentration. Compound 5 was inactive at all concentrations while all the others completely inhibited yeast proliferation at 100 μM. At 10 μM, Compound 6 was partially inhibitory and Compound 9 fully inhibited growth. Reduced concentrations of 9 were assayed to determine the lower range of activity (FIG. 1, panel 9*) of the compound. Compound 9 at 3 μM had a proliferation profile similar to that observed without inhibitor. In contrast, significant and reproducible inhibition was observed at 4 μM, and resulted in a lengthening of the time to half maximal growth by 1.8 times. The results from FIG. 1 are summarized in Table 2. Compounds 1, 2, 3 and 7 were not effective at doses up to and including 6 µM; higher doses (above 6 µM) have not been evaluated for these four compounds.

TABLE 2

Inhibition of yeast proliferation by 5 different synthesized compounds.

| Compound | 1 mM | 100 µM | 10 µM | 1 µM |
|---|---|---|---|---|
| 5 | − | − | − | − |
| 4 | i | + | − | − |
| 6 | + | + | +/− | − |
| 8 | i | + | − | − |
| 9 | + | + | + | − |

Concentrations of compounds are indicated.
(+) Complete inhibition (no proliferation); (−) no inhibition (normal proliferation); (+/−) partial inhibition; (i) compound insoluble.

Figure 2:
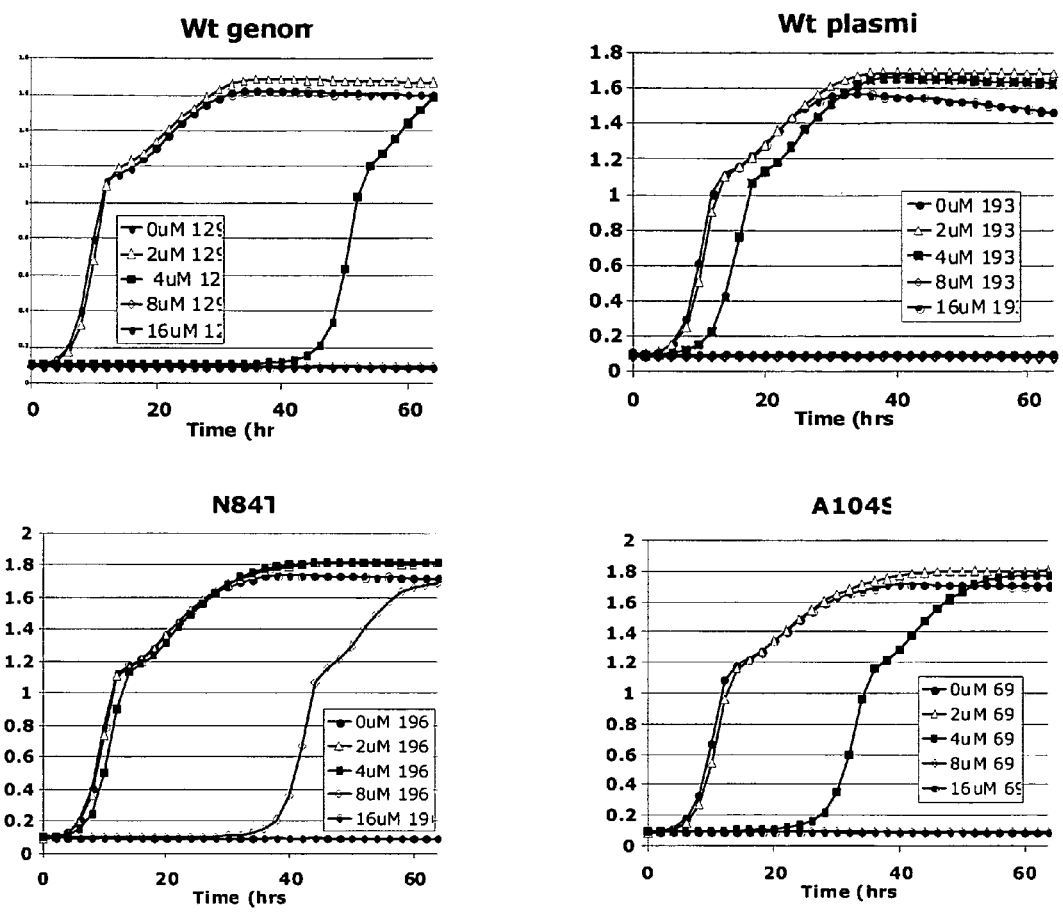
FIG. 2. Effects of Magmas mutations and expression on the inhibitory activity of compound 9 in yeast proliferation assay.

To demonstrate that effects of Compound 9 were mediated through Magmas, yeast strains containing several different Magmas mutations expressed on a plasmid were screened for alterations in the compound 9 concentration dependence. All of these stains express similar levels of Magmas protein, which is approximately 4 fold higher than the haploid control (Wt genomic). Comparing the dose response of Wt genomic, Wt plasmid showed that over-expression of Magmas reduces sensitivity of yeast to Compound 9 (FIG. 2). Yeast strains containing Magmas N84T (which is in the predicted binding region of the inhibitor) proliferate identically to Wt plasmid without SMI but had an increased resistance to Compound 9 as demonstrated by the shift in dose-response to the left. In contrast, A104S (which is not near the interaction site of Compound 9 with Magmas) resulted in an increased sensitivity of the yeast to inhibitor.

Cell lines were cultured with Compound 9, and it was observed that the morphological and biochemical features were similar to those in cells with siRNA-mediated reduced Magmas expression, providing additional evidence of target specificity.

Several Magmas SMI that are biologically active in yeast were synthesized. Over-expression of Magmas and the isolation of Magmas mutants with both increased and decreased sensitivity to Compound 9 demonstrated that Magmas is a target of this compound.

Compound 9 Binding to Magmas

Figures 3A, 3B:
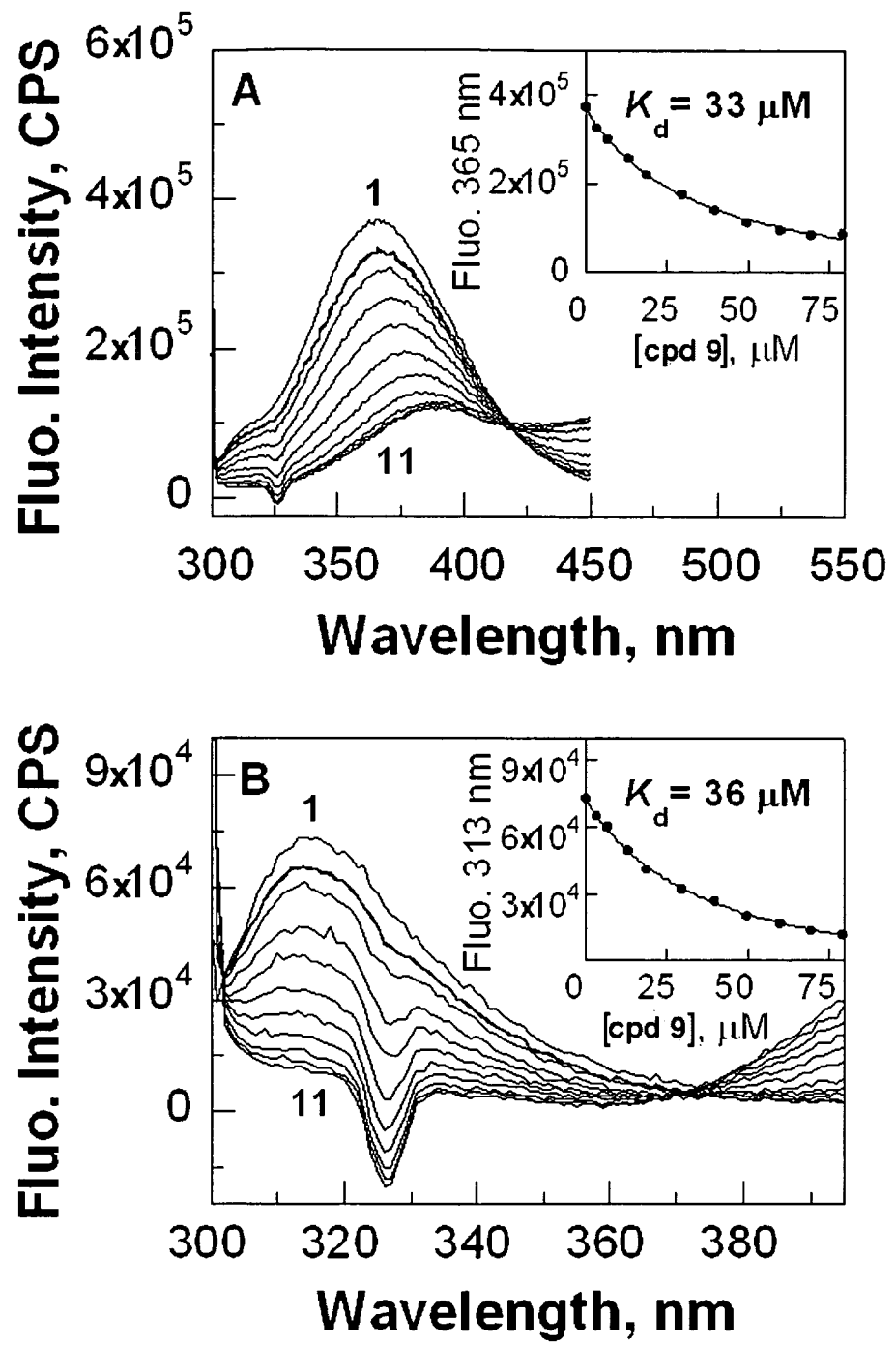
FIG. 3A-3B. Fluorescence intensity of Magmas (panel A, yeast; panel B, murine) at increasing concentrations of compound 9 (lines 1-11). Insert: Fluorescent intensity of Magmas at wavelength of peak intensity plotted as a function of concentration of compound 9, results in a calculated $K_d$ of 33 μM and 36 μm to yeast and murine Magmas, respectively.

The binding of Compound 9 to Magmas was also demonstrated using the technique of fluorescence emission spectrum. The binding of 9 to both purified yeast and mouse Magmas was evaluated. The fluorescence spectrum of tryptophan was measured for the binding to the yeast target and the fluorescence spectrum of tyrosine was measured for the binding to the murine target. The spectral shift observed at varying concentrations of 9 was used to determine the binding constant (FIG. 3).

The binding constants of 9 to the yeast and murine targets were similar at 34±2 µM and 36±2 µM, respectively. The human target was not evaluated, but since 121/125 amino acids in the human protein are identical to the murine protein, the results should not differ.

Compound 9 Inhibition of Mammalian Cells

Compound 9 was shown to differentially inhibit human cell lines and primary cells lines. Cell lines derived from human hematological malignancies and glioblastoma multiforme, and human umbilical vascular endothelial cells (HU-VEC) were cultured in standard media with the concentrations of 9 indicated in Table 3. Viable cells were scored by trypan blue dye exclusion at 48 hrs. The HUVEC population consisted of a pool of primary cells isolated from the blood vessels of 4 umbilical cords. Each cell type was tested in duplicate in at least three independent experiments. The data shows that the tumor cell lines were approximately 4 to 5-fold more sensitive to Compound 9 than the normal primary cells (HUVEC), consistent with the predicted clinical potential of Compound 9.

TABLE 3

Concentration effects of Compound 9 on viability of human cells.

| Cells | 0 | 2 um | 4 um | 6 um | 8 um | 12 um | 16 um | 20 um | 24 um |
|---|---|---|---|---|---|---|---|---|---|
| K562 | + | +/− | +/− | − | − | − | − | − | − |
| Karpas | + | +/− | +/− | +/− | − | − | − | − | − |
| Pfeiffer | + | +/− | +/− | − | − | − | − | − | − |
| Toledo | + | +/− | +/− | − | − | − | − | − | − |
| U87 | + | +/− | +/− | − | − | − | − | − | − |
| U118 | + | +/− | − | − | − | − | − | − | − |
| HUVEC | + | + | + | + | + | + | + | +/− | − |

(+) Viable,
(−) dead,
(+/−) partial viability.
K562: myeloid leukemia;
Karpas, Pfeiffer and Toledo: lymphoma;
U118 and U87: glioblastoma;
HUVEC: human umbilical vascular endothelial cells, (primary endothelial cells).

Effect of Compound 9 on Mitochondrial Activity

Figure 4A:
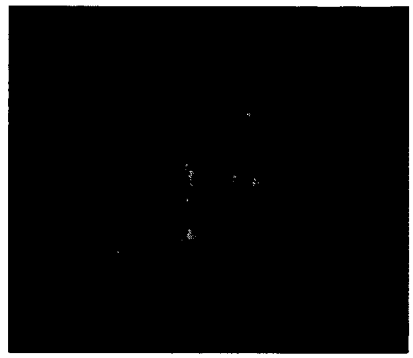
FIG. 4A-4B. Mitotracker Red intensity is reduced in HeLa cells incubated with Compound 9. Mitotracker Red intensity, indicated by the light grey area, confirms reduced mitochondrial activity in cells treated with the compound. A: cells without Compound 9; B: cells incubated with Compound 9.
Figure 4B:

HeLa cells were treated with 6 µM Compound 9 for 12 hours. The cells were then incubated with Mitotracker Red (100 nM) for 15 minutes, washed, fixed with formaldehyde, and examined by fluorescent microscopy. The results show that the Mitotracker Red intensity is reduced in cells incubated with 9 (FIG. 4B). This confirms that the invention affects mitochondrial activity.

Role of Magmas in Human Cancer (Osteosarcoma)

Osteosarcoma is characterized by osteoblast-like cells that produce osteoid and complex genetic abnormalities. Using a large tissue array linked to a clinical database, it was determined that normal osteoblasts do not express detectable amounts of Magmas using immunohistochemistry. However, 35% of more than 120 diagnostic osteosarcoma samples tested had very high Magmas expression. The results showed that Magmas expression was predictive of response to chemotherapy. Tumors with the lowest level of Magmas expression on diagnostic biopsy had the highest % of tumor necrosis at definitive resection. Microarray data from several independent laboratories showed that high Magmas mRNA expression similarly correlated with reduced survival in several solid tumors. Thus, Magmas inhibitors, as disclosed herein, may restore or enhance the sensitivity of cancers to standard chemotherapies.

Role of Magmas in Aging and Longevity

Cumulative oxidative stress is a major mechanism contributing to the aging process. Reactive oxygen species (ROS) generated from the mitochondrial respiratory chain progressively inflicts irreversible damage to cells, thereby reducing longevity. Impaired Magmas activity resulting from introduced mutations, siRNA mediated decreased protein expression or by Magmas inhibitor results in reduced oxidative phosphorylation and cell proliferation. By reducing cellular ROS and the resulting damage to rRNA and DNA, Magmas inhibition provides a beneficial means of influencing the aging process and potentially prolonging longevity.

Role of Magmas in Detecting Ischemic Injury

In stroke and post ischemic injuries to other tissues the majority of the irreversible damage occurs during the reperfusion of the affected area, which causes a rapid activation of multiple deleterious pathways. Included in cellular response to ischemia is an enhanced expression of Magmas. Central to the tissue injury is the role of mitochondria in generating reactive oxygen species, regulating membrane phospholipids composition and controlling apoptosis. Magmas inhibitor reduces the intensity of this reactive process by decreasing ROS formation, inhibiting the production of toxic phospholipids, preventing cytochrome c release and caspase activation, and secondarily lessens tissue inflammation, edema and damage. Detection of Magmas expression and its distribution pattern at hypoxic sites using trace labeled Magmas inhibitor allows quantification of the amount of tissue damage, and in addition could be used to evaluate the efficacy of other potential therapeutic interventions.

REFERENCES

1. Jubinsky P T, Messer A, Bender J, Morris R E, Ciraolo G M, Witte D P, Hawley R G, Short M K. Exp. Hematol. 29: 1392-1402, 2001.
2. Jubinsky P T, Short M K, Mutema G, Witte D P. J Histochem Cytochem. 51:585-596, 2003.
3. Peng J, Huang C- H, Short M K, Jubinsky P T. Magmas gene structure and evolution. In Silico Biol 5: 251-263, 2005, Epub 2005 Mar. 2
4. Jubinsky P T, Short M K, Mutema G, Morris R E, Ciraolo G M, Li M. J Mol Histol 36: 69-75, 2005.
5. Fernández-Mateos A, Mateos Burón L, Martín de la Nava E M, Rubio González R. J. Org. Chem. 68: 3585-3592, 2003.
6. Rosenberger M. and Neukom C. J. Org. Chem. 47: 1782-1785, 1982.
7. Waugh K M, Berlin K D, Ford W T, Holt E M, Carrol J P, Schomber P R, Thompson, M D, Schiffl L J. J. Med. Chem. 28: 116-124, 1985.
8. Sobol E, Bialer M, Yagen B. J. Med. Chem. 47: 4316-4326, 2004.
9. Laeckmann D, Rogister F, Dejardin J V, Prosperi-Meys C, Géczy J, Delarge J, Masereel B. Bioorg Med. Chem. 10:1793-804, 2002.
10. van de Vijver M J, He Y D, van't Veer L J, Dai H, Hart A A, Voskuil D W, Schreiber G J, Peterse J L, Roberts C, Marton M J, Parrish M, Atsma D, Witteveen A, Glas A, Delahaye L, van der Velde T, Bartelink H, Rodenhuis S, Rutgers E T, Friend S H, Bernards R. A gene-expression signature as a predictor of survival in breast cancer. N Engl J. Med. 347(25):1999-2009, 2002.
11. Desmedt C, Piette F, Loi S, Wang Y, Lallemand F, Haibe-Kains B, Viale G, Delorenzi M, Zhang Y, d'Assignies M S, Bergh J, Lidereau R, Ellis P, Harris A L, Klijn J G, Foekens J A, Cardoso F, Piccart M J, Buyse M, Sotiriou C; TRANSBIG Consortium. Strong time dependence of the 76-gene prognostic signature for node-negative breast cancer patients in the TRANSBIG multicenter independent validation series. Clin Cancer Res. 13(11):3207-14, 2007.

What is claimed is:

1. A compound of formula (I):

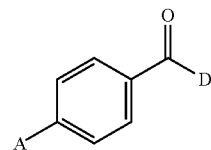

wherein A is

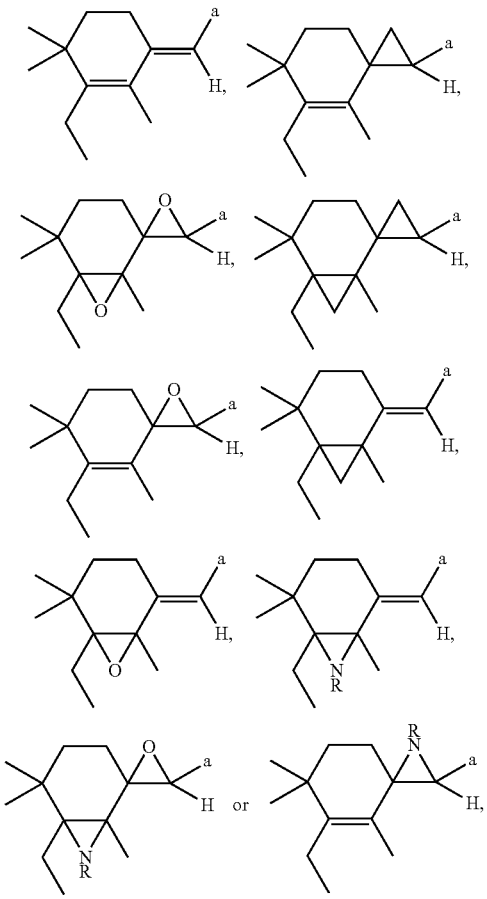

where "a" represents the point of attachment of A to the ring structure of formula (I) and where R is H, aliphatic, aromatic or heterocyclic; and wherein D is

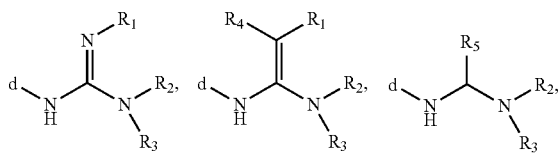

-continued

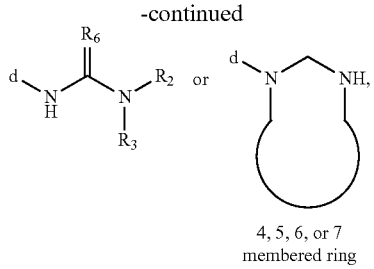

4, 5, 6, or 7
membered ring where "d" represents the point of attachment of D to the carbon atom of C=O of formula (I); where $R_1$, $R_2$, $R_3$, $R_4$ and $R_5$ are independently H, alkyl, aryl, phenyl, heteroaryl, arylalkyl, heterocyclic, alkenyl, allene, Br, Cl, I, F, OH, $NO_2$, $OCH_3$, $OC_2H_5$, O-alkyl, SH, S-alkyl, $NH_2$, or NH-alkyl; and where $R_6$ is C, O or S;
or a pharmaceutically acceptable salt thereof.

2. The compound of claim 1 having the formula:

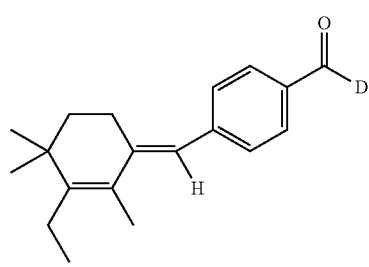 [SMILES: [2H]C(=O)c1ccc(/C=C2\CCC(C)(C)C(CC)=C2C)cc1]

or a pharmaceutically acceptable salt thereof.

3. The compound of claim 1 having the formula:

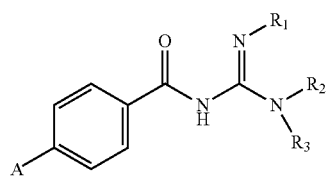

or a pharmaceutically acceptable salt thereof.

4. The compound of claim 1 having the formula:

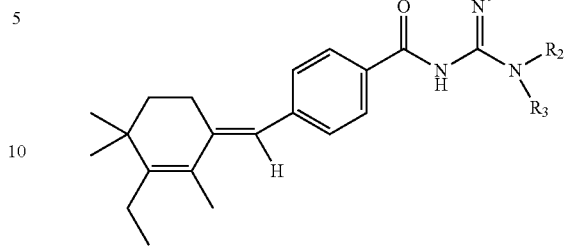

or a pharmaceutically acceptable salt thereof.

5. The compound of claim 1, wherein R=H.
6. The compound of claim 1, wherein alkyl is C1-C3 alkyl.
7. The compound of claim 1, wherein one or more of $R_1$, $R_2$, $R_3$, $R_4$ and $R_5$ is H.
8. The compound of claim 1 having the structure:

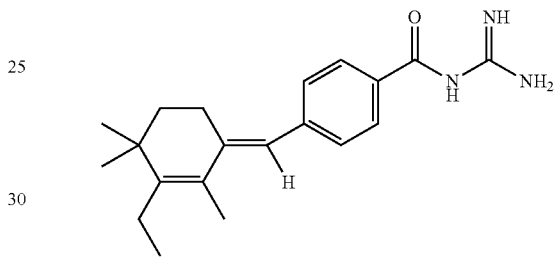

or a pharmaceutically acceptable salt thereof.
9. The compound of claim 1, wherein the compound is labeled with a detectable marker.
10. The compound of claim 9, wherein the detectable marker is a radioactive marker.
11. A pharmaceutical composition comprising the compound of claim 1 and a pharmaceutically acceptable carrier.
12. A method for detecting the expression of mitochondria-associated, granulocyte-macrophage colony stimulating factor signaling molecule (Magmas) in a tissue comprising contacting the tissue with the labeled compound of claim 9.
13. A method for inhibiting mitochondrial activity in a cell or tissue or for inhibiting metabolic activity in a cell or tissue comprising contacting the cell or tissue with the compound of claim 1.
14. A method of imaging ischemic injury in a subject comprising administering to the subject the compound of claim 9.

* * * * *